United States Patent
Itoh et al.

(10) Patent No.: US 8,575,384 B2
(45) Date of Patent: Nov. 5, 2013

(54) SILANOL-CONTAINING TRIARYLAMINE DERIVATIVES

(75) Inventors: Yusuke Itoh, Joetsu (JP); Ayumu Kiyomori, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 37 days.

(21) Appl. No.: 13/306,539

(22) Filed: Nov. 29, 2011

(65) Prior Publication Data

US 2012/0149913 A1   Jun. 14, 2012

(30) Foreign Application Priority Data

Nov. 30, 2010 (JP) .................................. 2010-266657
Jul. 21, 2011 (JP) .................................. 2011-159945

(51) Int. Cl.
*C07F 7/10* (2006.01)

(52) U.S. Cl.
USPC ........................................................ 556/479

(58) Field of Classification Search
USPC ........................................................ 556/479
See application file for complete search history.

(56) References Cited

U.S. PATENT DOCUMENTS

| | | |
|---|---|---|
| 3,180,730 A | 4/1965 | Klupfel et al. |
| 5,688,961 A | 11/1997 | Kushibiki et al. |
| 5,994,573 A | 11/1999 | Tachikawa et al. |

FOREIGN PATENT DOCUMENTS

| | | |
|---|---|---|
| EP | 0 517 542 A1 | 12/1992 |
| EP | 0 771 807 A1 | 5/1997 |
| JP | 58-065440 A | 4/1983 |
| JP | 4-346356 A | 12/1992 |
| JP | 7-110940 B | 11/1995 |
| JP | 4392869 B | 9/1999 |
| JP | 3614222 B | 11/2004 |

OTHER PUBLICATIONS

Search Report for European Application No. 11 00 9278 dated Feb. 21, 2012.

*Primary Examiner* — Shawquia Young
(74) *Attorney, Agent, or Firm* — Alston & Bird LLP

(57) ABSTRACT

Provided are triarylamine derivatives excellent in compatibility with various organic solvents or resins, capable of forming a silicon-oxygen bond on the surface of an inorganic material, and allowing easy purification; a preparation process of the triarylamine derivative; an intermediate product of the triarylamine derivative; an inorganic composite material obtained by bonding the triarylamine derivative to the surface of an inorganic material; and a preparation process of the inorganic composite material.

8 Claims, No Drawings

SILANOL-CONTAINING TRIARYLAMINE DERIVATIVES

BACKGROUND OF THE INVENTION

1. Field of the Invention

The present invention relates to novel silanol-containing triarylamine derivatives useful as a hole transporting material.

2. Description of the Related Art

Triarylamine derivatives have been used as a photoconductive material of electrophotographic photoreceptors. For example, U.S. Pat. No. 3,180,730 discloses a photoreceptor using a triphenylamine compound as a dye sensitizer. Japanese Patent Laid-Open No. 65440/1983 discloses a photoreceptor using a triarylamine derivative as a charge transporting material.

The triarylamine derivative disclosed in Japanese Patent Publication No. 110940/1995 is excellent as a hole transporting material and has been used for organic light emitting diode or organic thin-film solar cells. In the production of such devices by using a wet process, a solution obtained by dissolving the hole transporting material, together with an appropriate binder resin, in an organic solvent and the resulting solution is applied. As the binder resin, thermoplastic resins such as polycarbonate resin, polyester resin, acrylic resin, and polystyrene resin and thermosetting resins such as polyurethane resin and epoxy resin are considered.

Japanese Patent Laid-Open No. 346356/1992, on the other hand, discloses a method of using a resin obtained by dispersing a thermosetting polysiloxane resin in a thermoplastic resin as a component substance of a charge transporting material. Polysiloxane resins have characteristics which other resins do not have such as transparency, anti breakdown, light stability, and low surface tension. However, due to lack of compatibility with organic compounds, polysiloxane resins cannot be used singly as a component resin of a charge transporting material.

In order to solve these problems, Japanese Patent Nos. 3614222 and 4392869 disclose compounds having, in the triarylamine structure thereof, an alkoxysilyl group. These compounds are excellent in compatibility with a silicon-based resin such as polysiloxane and can provide a uniform organic thin film free of crystal precipitation or pin holes.

When an organic light emitting device is fabricated, a hole transporting material is usually stacked on an inorganic material. Due to the hydrolysis of an alkoxysilyl group, a silicon-oxygen bond is formed on the surface of the inorganic material, which is presumed to improve the transferring efficiency of charges on the interface.

The alkoxysilyl group disclosed in Japanese Patent Nos. 3614222 and 4392869 generate VOC (volatile organic component) upon hydrolysis, which causes the burden on the environment. In addition, for the hydrolysis of an alkoxysilane, a catalyst for accelerating the reaction is usually employed. The catalyst also serves to condense silanol groups and the reaction mixture inevitably becomes a mixture with a siloxane compound, which may possibly deteriorate the performance. Furthermore, when these alkoxysilanes are used as a hole transporting material, they are required to be purified highly. It is however difficult to purify them through distillation because they have a high boiling point. Using column chromatography for purification, on the other hand, may cause another problem that alkoxysilanes are easily hydrolyzed and adsorbed in the column.

There is therefore an eager demand for the development of a triarylamine derivative having more suitable properties as a hole transporting material.

SUMMARY OF THE INVENTION

An object of the present invention is to provide a triarylamine derivative excellent in compatibility with various organic solvents or resins, capable of forming a silicon-oxygen bond on the surface of an inorganic material, and allowing easy purification.

The present inventors have carried out an extensive investigation with a view to achieving the above-described object. As a result, it has been found that a novel triarylamine derivative having a silanol group at a specific position is excellent in compatibility with various organic solvents or resins and can be purified easily. It has also been found that this novel triarylamine derivative can be attached to the surface of an inorganic material in a convenient manner, leading to the completion of the present invention.

In one aspect of the present invention, there is provided a silanol-containing triarylamine derivative represented by formula (1):

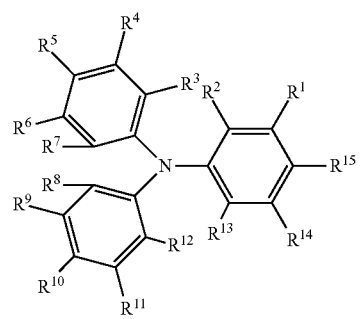

(1)

wherein, $R^1$ to $R^{15}$ each independently represents a substituent selected from diarylamino groups represented by formula (2), linear, branched or cyclic monovalent hydrocarbon groups (which may contain the diarylamino group represented by formula (2) as a substituent) having from 1 to 20 carbon atoms, alkoxy groups having from 1 to 20 carbon atoms, aryloxy groups having from 6 to 20 carbon atoms, halogen atoms, a hydrogen atom, and an amino group, with the proviso that at least one of $R^1$, $R^4$, $R^6$, $R^9$, $R^{11}$, and $R^{14}$ contains a substituent represented by the following formula: $SiR^{16}R^{17}OH$ wherein, $R^{16}$ and $R^{17}$ each independently represents a linear, branched, or cyclic monovalent hydrocarbon group having from 1 to 20 carbon atoms

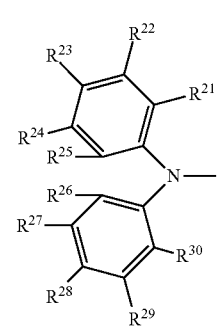

(2)

wherein, $R^{21}$, $R^{23}$, $R^{25}$, $R^{26}$, $R^{28}$, and $R^{30}$ each independently represents a substituent selected from linear, branched, or cyclic monovalent hydrocarbon groups having from 1 to 20 carbon atoms, alkoxy groups having from 1 to 20 carbon atoms, aryloxy groups having from 6 to 20 carbon atoms, halogen atoms, a hydrogen atom, and an amino group; $R^{22}$, $R^{24}$, $R^{27}$, and $R^{29}$ each independently represents a substituent selected from linear, branched, or cyclic monovalent hydrocarbon groups having from 1 to 20 carbon atoms, alkoxy groups having from 1 to 20 carbon atoms, aryloxy groups having from 6 to 20 carbon atoms, halogen atoms, a hydrogen atom, an amino group, and substituents represented by $SiR^{16}R^{17}OH$, with the proviso that without $R^{25}$ and $R^{26}$, carbon atoms at ortho positions with respect to the nitrogen atom may be coupled to form a carbazole ring structure.

In the above formula (1), either one or both of $R^{16}$ and $R^{17}$ each represents preferably a branched or cyclic monovalent hydrocarbon group having from 3 to 20 carbon atoms.

In another aspect of the present invention, there is also provided a preparation process of a silanol-containing triarylamine derivative represented by the above formula (1) comprising steps of reacting a compound represented by the below-described formula (3):

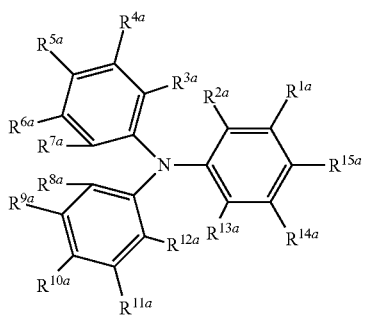

(3)

wherein, $R^{1a}$ to $R^{15a}$ have the same meanings as $R^1$ to $R^{15}$ in the formula (1), respectively, with the proviso that when any of $R^1$ to $R^{15}$ has $SiR^{16}R^{17}OH$, $R^{1a}$ to $R^{15a}$ corresponding thereto contains a halogen atom instead of $SiR^{16}R^{17}OH$ with a metal or an organic metal; and then reacting the reaction product thus obtained with a silicon reagent.

In a further aspect of the present invention, there is also provided an intermediate product of the silanol-containing triarylamine derivative of the above formula (1), which product is represented by the following formula (4):

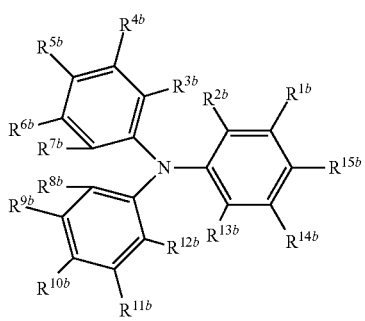

(4)

wherein, $R^{1b}$ to $R^{15b}$ have the same meanings as $R^1$ to $R^{15}$ in the formula (1), respectively, with the proviso that when any of $R^1$ to $R^{15}$ has a substituent represented by $SiR^{16}R^{17}OH$, $R^{1b}$ to $R^{15b}$ corresponding thereto contains $SiR^{16}R^{17}X$ (X=Cl or H) instead of $SiR^{16}R^{17}OH$.

In a still further aspect of the present invention, there is also provided an inorganic composite material obtained by bonding the silanol-containing triarylamine derivative represented by the above formula (1) to the surface of an inorganic material. The inorganic material is preferably a transparent conductive oxide.

In a still further aspect of the present invention, there is also provided a preparation process of an inorganic composite material including a step of contacting the silanol-containing triarylamine derivative represented by the formula (1) with an inorganic material.

The invention provides a novel silanol-containing triarylamine derivative. The triarylamine derivative of the present invention is excellent in compatibility with various organic solvents or resins and it can be purified easily. Due to such characteristics, the triarylamine derivative of the present invention is useful as a hole transporting material or hole injection material.

DETAILED DESCRIPTION OF THE INVENTION

The present invention will hereinafter be described more specifically by preferred embodiments. However, the present invention is by no means limited by the following description.

The silanol-containing triarylamine derivative in one aspect of the present invention is represented by the above formula (1). In the formula (1), $R^1$ to $R^{15}$ each independently represents a substituent selected from diarylamino groups represented by the formula (2), linear, branched, or cyclic monovalent hydrocarbon groups (which may contain, as a substituent thereof, the diarylamino group represented by the formula (2)) having from 1 to 20 carbon atoms, alkoxy groups having from 1 to 20 carbon atoms, aryloxy groups having from 6 to 20 carbon atoms, halogen atoms, a hydrogen atom, and an amino group, with the proviso that at least one of $R^1$, $R^4$, $R^6$, $R^9$, $R^{11}$, and $R^{14}$ contains a substituent represented by $SiR^{16}R^{17}OH$, wherein, $R^{16}$ and $R^{17}$ each represents a linear, branched, or cyclic monovalent hydrocarbon group having from 1 to 20 carbon atoms.

The diarylamino group which may constitute $R^1$ to $R^{15}$ in the formula (1) is represented by the above formula (2). In the formula (2), $R^{21}$ to $R^{30}$ each independently represents a substituent selected from linear, branched, or cyclic monovalent hydrocarbon groups having from 1 to 20 carbon atoms, alkoxy groups having from 1 to 20 carbon atoms, aryloxy groups having from 6 to 20 carbon atoms, halogen atoms, a hydrogen atom, an amino group, and substituents represented by $SiR^{16}R^{17}OH$, with the proviso that without $R^{25}$ and $R^{26}$, carbon atoms at ortho positions with respect to the nitrogen atom may be coupled to form a carbazole ring structure.

Examples of the monovalent hydrocarbon group having from 1 to 20 carbon atoms, which group may constitute $R^{21}$ to $R^{30}$, include linear alkyl groups such as methyl, ethyl, propyl, isopropyl, butyl, pentyl, hexyl, heptyl, octyl, nonyl, and decyl, branched alkyl groups such as isobutyl and tert-butyl, cyclic alkyl groups such as cyclopropyl, cyclobutyl, cyclopentyl, and cyclohexyl, alkenyl groups such as vinyl, allyl, propenyl, and butenyl, aryl groups such as phenyl and tolyl, and aralkyl groups such as 2-phenylethyl, 3-phenylpropyl, and 4-phenylbutyl.

Examples of the alkoxy group having from 1 to 20 carbon atoms, which group may constitute $R^{21}$ to $R^{30}$, include methoxy, ethoxy, butoxy, tert-butoxy, and hexyloxy groups. Examples of the aryloxy group having from 6 to 20 carbon atoms, which group may constitute $R^{21}$ to $R^{30}$, include phenoxy, p-methylphenoxy, and naphthoxy groups. Further examples of the substituent which may constitute $R^{21}$ to $R^{30}$ include halogen atoms such as fluorine atom, chlorine atom, bromine atom, and iodine atom, a hydrogen atom, and an amino group and in addition, $SiR^{16}R^{17}OH$, with the proviso that $SiR^{16}R^{17}OH$ constitutes any of the substituents $R^{22}$, $R^{24}$, $R^{27}$, and $R^{29}$ which are at meta position relative to the nitrogen atom.

In $SiR^{16}R^{17}OH$, $R^{16}$ and $R^{17}$ each independently represents a linear, branched, or cyclic monovalent hydrocarbon group having from 1 to 20 carbon atoms, preferably from 3 to 20 carbon atoms, more preferably from 3 to 10 carbon atoms and those similar to the monovalent hydrocarbon groups constituting $R^{21}$ to $R^{30}$ can be used. Of these, bulky substituents such as branched or cyclic alkyl groups having from 3 to 20 carbon atoms, aryl groups, and aralkyl groups are particularly preferred from the viewpoint of preventing dimerization of silanols due to dehydration condensation therebetween.

Specific examples of the substituent represented by $SiR^{16}R^{17}OH$ include, but not limited to, dimethylsilanol, diethylsilanol, diisopropylsilanol, di-sec-butylsilanol, dicyclopentylsilanol, dicyclohexylsilanol, tert-butylmethylsilanol, diphenylsilanol, and methylphenylsilanol.

The diarylamino group represented by the formula (2) may form a carbazole ring structure through coupling of the carbon atoms at ortho positions with respect to the nitrogen atom. At this time, neither $R^{25}$ nor $R^{26}$ is present.

Specific examples of the diarylamino group represented by the formula (2) include, but not limited to, diphenylamino, p-tolylphenylamino, m-tolylphenylamino, o-tolylphenylamino, di-p-tolylamino, di-m-tolylamino, p-methoxyphenylphenylamino, m-methoxyphenylphenylamino, o-methoxyphenylphenylamino, carbazolyl, and 3-methoxycarbazolyl groups.

As examples of the linear, branched, or cyclic monovalent hydrocarbon group having from 1 to 20 carbon atoms, which group may constitute $R^1$ to $R^{15}$ in the formula (1), monovalent hydrocarbon groups similar to those described in $R^{21}$ to $R^{30}$ can be given.

The linear, branched, or cyclic monovalent hydrocarbon groups having from 1 to 20 carbon atoms, which may constitute $R^1$ to $R^{15}$, may contain a diarylamino group represented by the formula (2).

Examples of the alkoxy groups having from 1 to 20 carbon atoms, which groups may constitute $R^1$ to $R^{15}$, include methoxy, ethoxy, butoxy, tert-butoxy, and hexyloxy groups.

Examples of the aryloxy groups having from 6 to 20 carbon atoms, which groups may constitute $R^1$ to $R^{15}$, include phenoxy, p-methylphenoxy, and naphthoxy groups.

Examples of the substituent which may constitute $R^1$ to $R^{15}$ include halogen atoms such as fluorine, chlorine, bromine and iodine, a hydrogen atom, and an amino group.

In the formula (1), at least one of $R^1$, $R^4$, $R^6$, $R^9$, $R^{11}$, and $R^{14}$ contains the substituent represented by $SiR^{16}R^{17}OH$, because when the triarylamine derivative of the present aspect is used as a photoconductive material, the $SiR^{16}R^{17}OH$ group can form a silicon-oxygen bond on the surface of an inorganic material. In the present embodiment, at least one of $R^1$, $R^4$, $R^6$, $R^9$, $R^{11}$, and $R^{14}$ may be the substituent represented by $SiR^{16}R^{17}OH$. Alternatively, at least one of $R^1$, $R^4$, $R^6$, $R^9$, $R^{11}$, and $R^{14}$ may be the substituent represented by the formula (2) or may have the substituent represented by the formula (2) and at the same time, contain the substituent represented by $SiR^{16}R^{17}OH$ as any of $R^{22}$, $R^{24}$, $R^{27}$, and $R^{29}$ in the formula (2)

Preferably, the compound represented by the formula (1) contains one or two substituents represented by $SiR^{16}R^{17}OH$, because when it contains more than two such substituents, bulkiness may increase, resulting in a decrease in an adsorption amount to the surface of an inorganic material per unit area.

Of the triarylamine derivative compounds represented by the formula (1), the following compounds are particularly preferred.

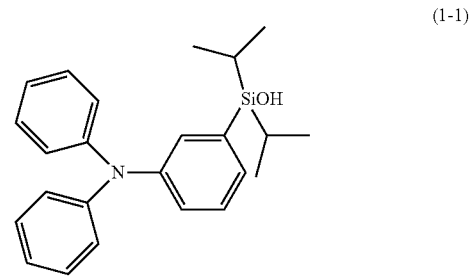

(1-1)

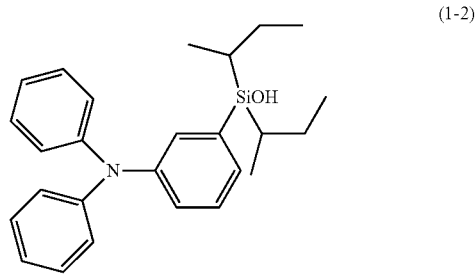

(1-2)

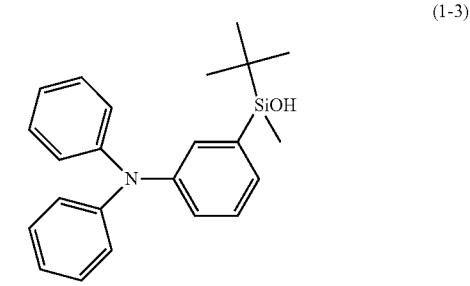

(1-3)

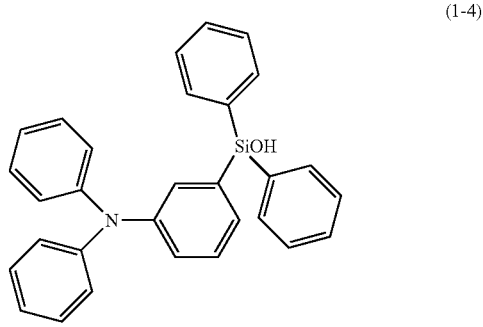

(1-4)

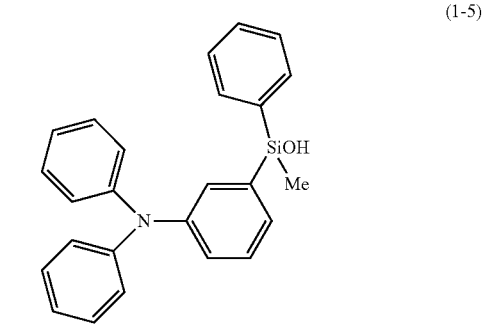

(1-5)

(1-6)
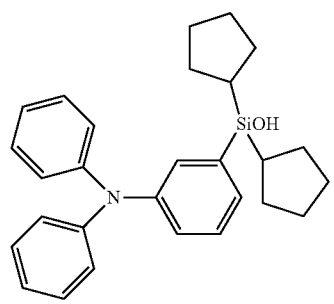
(1-10)
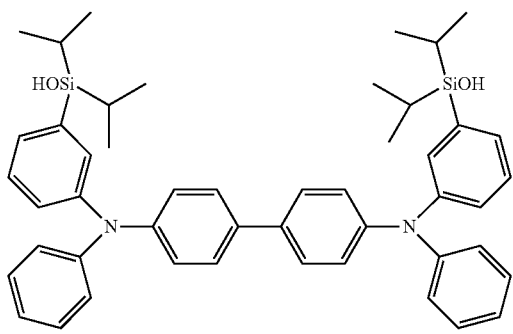
(1-7)
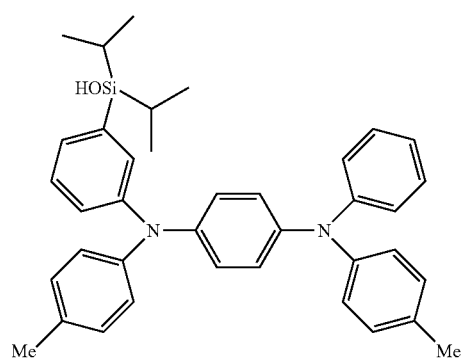
(1-11)
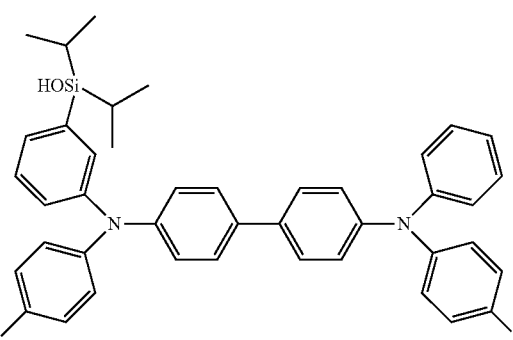
(1-8)
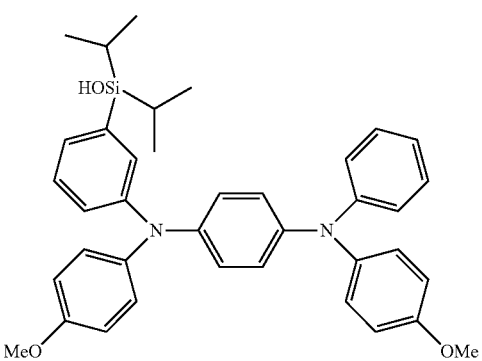
(1-12)
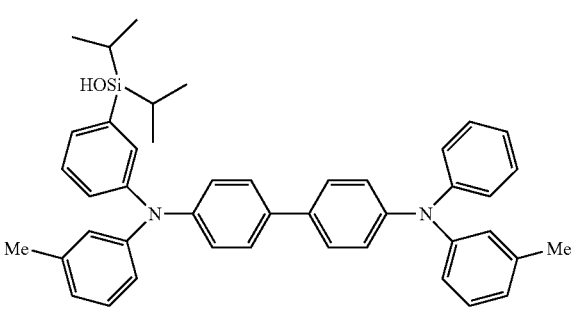
(1-9)
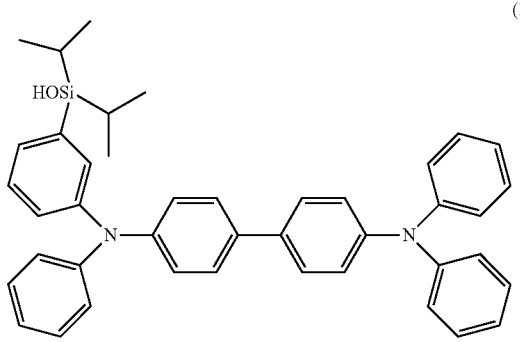
(1-13)
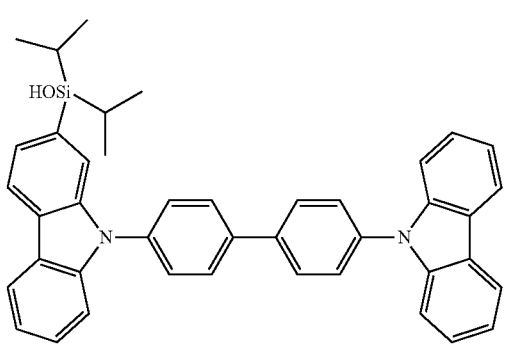

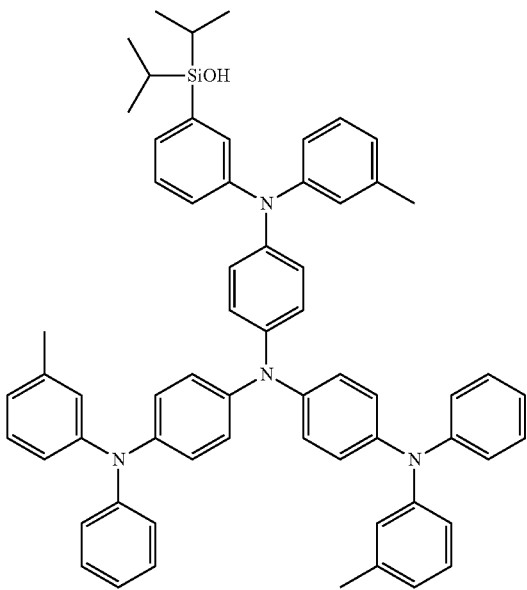

(1-14)

Another aspect of the present invention, that is, the preparation process of a silanol-containing triarylamine derivative represented by the above formula (1) will be described. The triarylamine derivative can be prepared by a process comprising a step of reacting the compound represented by the above formula (3) with a metal or an organic metal and a step of reacting the reaction product thus obtained with a silicon reagent.

The starting material is represented by the formula (3). In the formula (3), $R^{1a}$ to $R^{15a}$ have the same meanings as $R^1$ to $R^{15}$ defined in the formula (1), respectively. When the compound represented by the formula (1), which is an objective substance, contains a group represented by $SiR^{16}R^{17}OH$ as any of $R^1$ to $R^{15}$, $R^{1a}$ to $R^{15a}$ corresponding to the group contains a halogen atom such as chlorine, bromine, or iodine instead of a substituent represented by $SiR^{16}R^{17}OH$.

This means that at least one of $R^{1a}$, $R^{4a}$, $R^{6a}$, $R^{9a}$, $R^{11a}$, and $R^{14a}$ contains a halogen atom. When at least one of $R^{1a}$, $R^{4a}$, $R^{6a}$, $R^{9a}$, $R^{11a}$, and $R^{14a}$ contains a halogen atom or when the compound represented by the formula (1), which is an objective substance, has the substituent represented by the formula (2) and at the same time, any of the substituents $R^{22}$, $R^{24}$, $R^{27}$, and $R^{29}$ in the formula (2) is $SiR^{16}R^{17}OH$, any of the substituents corresponding to $R^{22}$, $R^{24}$, $R^{27}$, and $R^{29}$ of the diarylamino group in the compound of the formula (3), which is a starting material, may be a halogen atom.

The compound of the formula (3) which is a starting material can be obtained by the Ullmann condensation reaction between diphenylamine and an aryl halide.

Examples of a metal to be reacted in the step of reacting the compound represented by the above formula (3) with a metal or an organic metal include metal lithium and metal magnesium. Examples of the organic metals include n-butyl lithium, sec-butyl lithium, tert-butyl lithium, methyl lithium, phenyl lithium, methyl magnesium chloride, and methyl magnesium bromide.

The amount of the metal or organic metal to be used for the reaction is preferably from 1 to 10 mol, more preferably from 1 to 1.5 mol, relative to the compound of the formula (3). The reaction temperature upon this reaction is preferably from −100° C. to 100° C., more preferably from −80° C. to −30° C. when an organolithium reagent is used for the reaction. When an organomagnesium reagent or the metal is used for the reaction, on the other hand, the reaction temperature is preferably from 0° C. to 200° C., more preferably from 20° C. to 100° C. The reaction time is preferably from 30 minutes to 50 hours, more preferably from 1 hour to 20 hours. As the solvent, ether-based solvents and hydrocarbon-based solvents are preferred. Specific examples of the solvent include diethyl ether, tetrahydrofuran, hexane, pentane, toluene, and xylene, and mixed solvents thereof.

Then, a step of reacting the reaction product obtained by the above-described step with a silicon reagent is performed. In this step, the reaction product is reacted with a silicon reagent to prepare the compound represented by the formula (1). The silicon reagent serves to introduce the substituent $SiR^{16}R^{17}OH$ in the compound represented by the formula (1). The silicon reagent can be represented by $R^{16}R^{17}SiY_aH_b$ (wherein, $R^{16}$ and $R^{17}$ have the same meanings as $R^{16}$ and $R^{17}$ defined in the formula (1), respectively, Y represents Cl or $OR^{18}$ in which $R^{18}$ represents a linear or branched alkyl group having from 1 to 10 carbon atoms, a=1 or 2, and a+b=2. Thus, a silicon reagent having a structure with desired $R^{16}$ and $R^{17}$ can be used.

Specific examples of the silicon reagent include, but not limited to, diisopropylchlorosilane, diisopropyldichlorosilane, di-sec-butylchlorosilane, dicyclopentyldichlorosilane, dicyclohexyldichlorosilane, tert-butylmethylchlorosilane, diphenyldichlorosilane, methylphenylchlorosilane, diisopropyldimethoxysilane, di-sec-butylmethoxysilane, dicyclopentyldimethoxysilane, dicyclohexyldimethoxysilane, tert-butylmethylmethoxysilane, diphenyldimethoxysilane, and methylphenylmethoxysilane.

The amount of the silicon reagent to be used in the reaction is preferably from 1 to 10 mols, more preferably from 1 to 2 mol, per mol of the compound represented by the formula (3). The reaction temperature of the above-described reaction is preferably from −100° C. to 100° C., more preferably from 0° C. to 20° C. The reaction time in this step is preferably from 30 minutes to 50 hours, more preferably from 1 to 20 hours. The reaction temperature and time can be determined as needed by those skilled in the art. As the solvent, ether-based solvents and hydrocarbon-based solvents are preferred. Specific examples of the solvent include diethyl ether, tetrahydrofuran, hexane, pentane, toluene, and xylene, and mixed solvents thereof.

After the reaction with the silicon reagent, the intermediate product thus obtained is reacted further to convert it into silanol. The intermediate product is represented by the above formula (4). In the formula (4), $R^{1b}$ to $R^{15b}$ have the same meanings as $R^1$ to $R^{15}$ of the formula (1), respectively. When any of $R^1$ to $R^{15}$ contains a substituent represented by $SiR^{16}R^{17}OH$, $R^{1b}$ to $R^{15b}$ corresponding to it contains, instead of $SiR^{16}R^{17}OH$, $SiR^{16}R^{17}X$ (X=Cl or H). This means that at least one of $R^{1b}$, $R^{4b}$, $R^{6b}$, $R^{9b}$, $R^{1b}$, and $R^{14b}$ may be $SiR^{16}R^{17}X$. When the compound represented by the formula (1), which is an objective substance, has a substituent represented by the above formula (2) and at the same time, any of the substituents $R^{22}$, $R^{24}$, $R^{27}$, and $R^{29}$ in the formula (2) is $SiR^{16}R^{17}OH$, any of the substituents of the diarylamino group, in the compound of the formula (4) which is an intermediate product, corresponding to $R^{22}$, $R^{24}$, $R^{27}$, and $R^{29}$ is $SiR^{16}R^{17}X$.

The intermediate product represented by the formula (4) can also be used, after isolation of it from the reaction mixture, for a subsequent step which will be conducted after the elapse of certain time or at another place. Alternatively, the reaction mixture containing the intermediate product may be provided for the subsequent step as is.

When for the compound of the formula (3), a silicon reagent such as diisopropyldichlorosilane, dicyclopentyldichlorosilane, dicyclohexyldichlorosilane, diphenyldichlorosilane, diisopropyldimethoxysilane, dicyclopentyldimethoxysilane, dicyclohexyldimethoxysilane, or diphenyldimethoxysilane is used, chlorosilane or ester silane can be obtained as the intermediate product represented by the formula (4). When the intermediate product is chlorosilane or ester silane, silanol can be obtained by adding water to the reaction mixture to cause hydrolysis.

When for the compound of the formula (3), a silicon reagent such as diisopropylchlorosilane, di-sec-butylchlorosilane, tert-butylmethylchlorosilane, methylphenylchlorosilane, di-sec-butylmethoxysilane, tert-butylmethylmethoxysilane or methylphenylmethoxysilane, hydroxysilane can be obtained as the intermediate product represented by the formula (4). When hydroxysilane is produced as the intermediate product, silanol can be obtained by adding water to the intermediate product in the presence of a metal catalyst or a basic catalyst to oxidize it. Examples of the metal catalyst include palladium on activated charcoal, palladium acetate, ruthenium on activated charcoal, and triruthenium dodecacarbonyl. Examples of the basic catalyst include sodium hydroxide, potassium hydroxide, sodium ethoxide, and sodium methoxide. The amount of such a catalyst to be used in the reaction is preferably from 0.0001 to 10 mol, particularly preferably from 0.001 to 1 mol, relative to the compound of the formula (3). The reaction temperature of the silanol forming reaction is preferably from 0° C. to 200° C., particularly preferably from 0° C. to 100° C. The reaction time is preferably from 30 minutes to 30 hours, particularly preferably from 1 hour to 20 hours. As the solvent, ether-based solvents, hydrocarbon-based solvents, and alcohol-based solvents are preferred. Examples include diethyl ether, tetrahydrofuran, hexane, pentane, toluene, xylene, methanol, ethanol, isopropanol, and butanol, and mixed solvents thereof.

The silanol-containing triarylamine derivative thus obtained can be purified further. Examples of the purification method include, but not limited to, HPLC and silica gel chromatography. The triarylamine derivative according to the present aspect is advantageous particularly for ease of purification.

According to a further aspect, the present invention provides an inorganic composite material obtained by attaching the silanol-containing triarylamine derivative represented by the formula (1) to the surface of an inorganic material. A description will next be made on this inorganic composite material.

The inorganic material in the present aspect is not limited. Examples include metals such as silicon, germanium, gallium, indium, iron, nickel, copper, cobalt, chromium, molybdenum, ruthenium, silver, brass, and stainless steel; metal oxides such as silicon oxide, germanium oxide, titanium oxide, zinc oxide, zirconium oxide, tin oxide, aluminum oxide, magnesium oxide, indium oxide, barium titanate, lead zirconate titanate, indium tin oxide, aluminum zinc oxide, indium zinc oxide, indium gallium zinc oxide, and fluorine-doped tin oxide; and glasses such as soda lime glass and borosilicate glass. Of these, transparent conductive oxides such as indium tin oxide, indium zinc oxide, aluminum zinc oxide, zinc oxide, indium gallium zinc oxide, and fluorine-doped tin oxide are preferred, with indium tin oxide being particularly preferred.

The inorganic material is not limited insofar as it is a solid material. In particular, it may take any shape and it may be, for example, plate-like, spherical, disk-shaped, particulate, or porous. The shape is not limited to the above-exemplified one. The surface shape of the solid material is also not limited and it may have a planar surface, a curved surface, a micro structure, or a nano structure. The surface shape is not limited to the above-exemplified ones. When the inorganic material is porous, the surface means a place which is measured using the BET specific surface area measurement method and to which molecules can be physically adsorbed.

The inorganic composite material according to the present aspect is obtained by forming a covalent bond by reacting the silanol group of the triarylamine derivative represented by the formula (1) with a reactive group present on the surface of the inorganic material. In other words, it is an inorganic composite material in which the silanol-containing triarylamine derivative is covalently bonded to the surface of the inorganic material via an Si—O bond.

The reactive group on the surface of the inorganic material is not limited insofar as it can react with the silanol group of the triarylamine derivative represented by the formula (1). Examples of the reactive group include a mercapto group, an amino group, a hydroxyl group, alkoxy groups having from 1 to 10 carbon atoms, and an isocyanate group. It is preferably a hydroxyl group.

In the inorganic composite material according to the present aspect, the triarylamine derivative may be bonded to either the entirety of the surface of the inorganic material or only a portion of the surface of the inorganic material.

The inorganic composite material obtained by bonding the silanol-containing triarylamine derivative to the surface of the inorganic material according to the present mode can be used advantageously in the fabrication of an organic electroluminescent element. Such an inorganic composite material is particularly useful because a transfer efficiency of charges on the interface is improved by the silicon-oxygen bond formed on the surface of the inorganic material.

The inorganic composite material according to the present aspect will next be described from the standpoint of its preparation process. The preparation process of the inorganic composite material comprises a step of hydrophilizing an inorganic material, a step of contacting the silanol-containing triarylamine derivative represented by the formula (1) with the inorganic material, and optionally a step of forming a bond between the triarylamine derivative and the inorganic material.

The type and the shape of the inorganic material serving as a starting material have already been described above. When the inorganic material has on the surface thereof a reactive group, typically a hydroxyl group, it can be used as is in the step of contacting it with the triarylamine derivative without giving any pretreatment to the inorganic material. When the inorganic material has no hydroxyl group or does not have abundant hydroxyl groups on the surface thereof, on the other hand, it is preferred to carry out the hydrophilizing step in order to increase the number of reaction sites. As the hydrophilizing treatment, a conventionally known treatment can be employed. The number of surface hydroxyl groups can be increased by oxidatively hydrophilizing the surface of the inorganic material by a dry treatment such as oxygen plasma treatment, corona treatment, or UV ozone treatment or a wet treatment with a piranha solution (sulfuric acid—aqueous hydrogen peroxide). Alternatively, the number of reaction sites can be increased by providing an inorganic thin-film layer such as silicon oxide on the surface by using thermal oxidation, CVD, or sputtering. Thus, it can be said that the step of hydrophilizing an inorganic material is an optional pretreatment step. The preparation process of an inorganic composite material does not always include this step.

The step of contacting the silanol-containing triarylamine derivative represented by the formula (1) with the inorganic material can be carried out in any manner. For example, a solution process using a solution of the compound of the formula (1) can be given as one example of this step. In the solution process, the contacting step includes a step of preparing a solution of the triarylamine derivative represented by the formula (1) and a step selected from (a) a step of dipping the inorganic material in the solution to apply it to the surface, (b) a step of applying the solution to the surface of the inorganic material by a technique such as spin coating or spray coating, and (c) a step transferring the solution to the surface of the inorganic material by a technique such as micro contact printing. As well as the above-described step (a), (b), or (c), a typical method of contacting the solution with the surface of the inorganic material can be employed. The solution of the triarylamine derivative is prepared preferably by dissolving the triarylamine derivative in a solvent such as toluene, xylene, mesitylene, chloroform, acetonitrile, or benzonitrile to give its concentration of from 0.001 to 100 mM, preferably from 0.01 to 10 mM. The concentration is adjusted to fall within the above-described range to sufficiently react the triarylamine derivative with an active group, particularly a hydroxyl group, on the surface of the inorganic material.

An alternative process is a gas phase process in which the vapor of the triarylamine derivative of the formula (1) is contacted with the inorganic material. Examples of the gas phase process include a process comprising a step of evaporating the compound represented by the formula (1) in a reaction chamber and a step of adsorbing the compound represented by the formula (1) to the surface of the inorganic material which is allowed to coexist in the chamber. In the gas phase process, the vapor pressure of the triarylamine derivative in the reaction chamber is preferably controlled to from $10^{-6}$ to $10^{-2}$ Pa.

Either of the solution process or the gas phase process can be carried out at any temperature. The temperature can be selected, depending on the properties of the inorganic material or the properties of the triarylamine derivative represented by the formula (1). For example, a temperature range from 0 to 300° C. is preferred, but not limited thereto. In addition, the triarylamine derivative and the inorganic material can be contacted under any pressure, but the solution process is performed particularly preferably under normal pressure or under increased pressure. The gas phase process is, on the other hand, performed particularly preferably under reduced pressure.

The step of forming a bond may be carried out simultaneously with the contacting step or the bond formation step may be performed after the contacting step. When the bond formation step is performed after the contacting step, the bond can be formed at any temperature. Although the temperature can be selected, depending on the properties of the inorganic material or the properties of the triarylamine derivative represented by the formula (1), a temperature range from 0 to 300° C. is preferred. For example, when the contacting step is performed at normal temperature by using the solution process, the bond formation step may be performed, after evaporation of the solvent, by heating the inorganic material, to which the triarylamine derivative has been contacted, at from 20 to 250° C., preferably from 40 to 200° C. for from about 1 to 120 minutes. The inorganic material can be heated using an ordinarily employed heater or hot plate.

The triarylamine derivative of the present invention represented by the formula (1) is particularly advantageous because it can be coupled with the inorganic material without a catalyst. It is convenient and preferred to form a bond with the inorganic material in the absence of a catalyst. The bond formation step may however be performed in the presence of a catalyst as needed. When a catalyst is used, it is possible to form a bond by applying the catalyst after the contacting step or carry out these two steps simultaneously while allowing the catalyst to co-exist in the contacting step. A variety of acidic or basic substances can be used as the catalyst. Specific examples include Bronsted acids such as hydrochloric acid, sulfuric acid, nitric acid, acetic acid, phosphoric acid, formic acid, trifluoroacetic acid, methanesulfonic acid, trifluoromethanesulfonic acid, dodecylbenzenesulfonic acid, and paratoluenesulfonic acid; Lewis acids such as titanium tetrachloride, aluminum chloride, iron chloride, tin chloride, zinc chloride, dibutyltin dilaurate, titanium tetraisopropoxide, boron trichloride, tris(pentafluorophenyl)borane, yttrium triflate, ytterbium triflate, trimethylsilyl triflate, and tert-butyldimethylsilyl triflate; solid acids such as activated clay and cation exchange resin; alkali metal salts such as sodium hydroxide, lithium hydroxide, potassium hydroxide, rubidium hydroxide, cesium hydroxide, sodium methoxide, sodium ethoxide, potassium methoxide, sodium phenoxide, potassium tert-butoxide, sodium carbonate, potassium carbonate, cesium carbonate, sodium hydrogen carbonate, potassium hydrogen sulfate, potassium phosphate, and sodium dihydrogen phosphate; alkaline earth metal salts such as magnesium hydroxide, calcium hydroxide, barium hydroxide, strontium hydroxide, magnesium oxide, and calcium oxide; metal oxides such as aluminum oxide, tin oxide, zinc oxide, zirconium oxide, titanium oxide, yttrium oxide, and scandium oxide; nitrogen compounds such as ammonia, trimethylamine, diethylamine, triethylamine, tributylamine, pyrrolidine, piperidine, piperazine, 1,4-diazabicyclo[2.2.2]octane, 1,8-diazabicyclo[5.4.0]undecene, hexamethylenetetramine, and guanidine; and onium salts such as ammonium chloride, ammonium sulfate, triethylamine trifluoromethanesulfonate, pyridine hydrochloride, tributylphosphonium tetrafluoroborate, tetramethylammonium hydroxide, and tetrabutylammonium hydroxide. The catalyst is used in any amount and the amount can be determined, depending on the bond formation rate. It is however preferred to add it so that a molar ratio of the catalyst to the triarylamine derivative represented by the formula (1) will be from 0.0001 to 10.

After the contacting step and the optional bond formation step, a post-treatment step may be carried out as needed. The post-treatment step may include a step of subjecting the resulting inorganic composite material to an ultrasonic treatment to remove the triarylamine derivative which has not bonded. In addition, it may comprise a step of cleaning with an arbitrary solvent such as ethanol or toluene; a step of removing a volatile component by heating; a step of drying or removing a volatile component under reduced pressure; or a step using some of these steps in combination.

The above-described preparation process is advantageous because an inorganic composite material advantageously usable in the preparation of an organic electroluminescent element can be prepared simply and conveniently.

The invention will next be described more specifically by examples. It should however be borne in mind that the present invention is not limited by them.

EXAMPLES

Example 1

Synthesis of m-(hydroxydiisopropylsilyl)phenyldiphenylamine [Compound (1-1)]

In a nitrogen atmosphere, 2.0 ml (3.34 mmol) of 1.67 mM n-butyl lithium was added to 976.0 mg (3.01 mmol) of m-bromotriphenylamine at □78° C. in a tetrahydrofuran solvent, followed by stirring for 30 minutes. Then, 881.3 mg (4.79 mmol) of diisopropyldichlorosilane was added. The resulting mixture was heated gradually and stirred overnight. After water and toluene were added to the solution thus obtained, the organic layer was extracted from the resulting mixture by a separating operation. The solution thus obtained was dried over magnesium sulfate and concentrated under reduced pressure by using a rotary evaporator. The residue was purified using HPLC to yield 950.6 mg (2.53 mmol) of a yellow liquid in a yield of 84.1%. It was confirmed as a result of measurement of GC-MS spectrum that the liquid thus obtained was m-(hydroxydiisopropylsilyl)phenyldiphenylamine.

GC-MS m/z: 375 ($M^+$)

Example 2

Synthesis of N,N'-bis(m-diisopropylhydroxysilylphenyl)-N,N'-diphenylbenzidine [Compound (1-10)]

In a nitrogen atmosphere, 1.5 ml (2.48 mmol) of 1.65 mM n-butyl lithium was added to 654.2 mg (1.01 mmol) of N,N'-bis(m-bromophenyl)-N,N'-diphenylbenzidine at □78° C. in a tetrahydrofuran solvent, followed by stirring for 30 minutes. Then, 743.9 mg (4.04 mmol) of diisopropyldichlorosilane was added. The resulting mixture was heated gradually and stirred overnight. After water and toluene were added to the solution thus obtained, the organic layer was extracted by a separating operation. The solution thus obtained was dried over magnesium sulfate and concentrated under reduced pressure by using a rotary evaporator. The residue was purified using HPLC and GPC to yield 365.9 mg (0.49 mmol) of a colorless liquid in a yield of 48.4%. It was confirmed as a result of measurement of MALDI-TOFMS spectrum that the liquid thus obtained was N,N'-bis(m-diisopropylhydroxysilylphenyl)-N,N'-diphenylbenzidine.

$^1$H-NMR (600 MHz, din $CDCl_3$): 0.91 (d, J=7.3 Hz, 12H), 1.00 (d, J=7.3 Hz, 12H), 1.12 (sept, J=7.3 Hz, 2H), 6.98 (t, J=6.9 Hz, 2H), 7.05-7.15 (m, 10H), 7.17-7.27 (m, 10H), 7.29 (a, 2H), 7.41 (d, J=7.8 Hz, 4H)

MALDI-TOFMS m/z: 749 ($M^+$)

Example 3

Preparation of glass having m-(hydroxydiisopropylsilyl)phenyldiphenylamine [Compound (1-1)] bonded to the surface thereof The m-(hydroxydiisopropylsilyl)phenyldiphenylamine synthesized in Example 1 was mixed with acetonitrile to prepare a colorless and transparent 1 mM acetonitrile solution. A slide glass having a surface subjected to an UV ozone treatment for 10 minutes was dipped in the resulting solution for 3 minutes and withdrawn. The solvent was then evaporated. Next, after the resulting slide glass was heated for 5 minutes on a hot plate of 180° C., it was cooled to room temperature. Ultrasonic cleaning was carried out in 0.25 mmol/L sulfuric acid/ethanol to remove the compound 1-1 which had not bonded to the substrate. Ultrasonic cleaning was performed for further 5 minutes in ethanol and nitrogen was sprayed to the slide glass at room temperature to dry it.

Results of the X-ray photoelectron spectroscopy (XPS) measurement of the surface of the glass sample thus obtained are shown in Table 1. In Table 1, the term "untreated glass" means a glass having a surface subjected to an UV ozone treatment but not subjected to a treatment for bonding Compound 1-1 to the surface of the glass. Compared with the untreated glass, ratios of nitrogen and carbon derived from Compound 1-1 increase on the surface of the glass prepared in Example 2, meaning that Compound 1-1 has bonded to the glass surface. Compared with silicon on the surface of the untreated glass, a ratio of silicon on the surface of the glass prepared in Example 3 is smaller than silicon on the surface of the untreated glass, which means that abundant silicon derived from glass is present on the untreated glass surface.

TABLE 1

| Sample | Oxygen | Nitrogen | Carbon | Silicon | Total |
|---|---|---|---|---|---|
| (unit: atomic %) | | | | | |
| Example 3 | 57.9 | 0.9 | 14.3 | 26.9 | 100.0 |
| Untreated glass | 69.7 | 0.2 | 2.2 | 27.9 | 100.0 |

Example 4

Preparation of an ITO film-coated glass having m-(hydroxydiisopropylsilyl)phenydiphenylamine [Compound (1-1)] bonded to the surface thereof The m-(hydroxydiisopropylsilyl)phenyldiphenylamine synthesized in Example 1 was mixed with acetonitrile to prepare a colorless and transparent 1 mM acetonitrile solution. An ITO (indium tin oxide) film-coated glass having a surface subjected to an UV ozone treatment for 10 minutes was dipped in the resulting acetonitrile solution for 3 minutes and then, withdrawn. The solvent was thereafter evaporated. Next, after the resulting ITO film-coated glass was heated for 10 minutes on a hot plate of 180° C., it was cooled to room temperature. Ultrasonic cleaning was carried out in 0.25 mmol/L sulfuric acid/ethanol for 15 minutes to remove Compound 1-1 which had not bonded to the substrate. Ultrasonic cleaning was performed for further 5 minutes in ethanol and nitrogen was sprayed to the glass at room temperature to dry it. The results of XPS measurement of the surface of the sample are shown in Table 2.

In Table 2, the term "untreated ITO glass" means an ITO film coated glass having a surface subjected to an UV ozone treatment but not subjected to a treatment for bonding Compound 1-1 to the surface. Compared with the untreated ITO glass, ratios of nitrogen, carbon, and silicon derived from Compound 1-1 increase and a ratio of indium derived from ITO decreases on the surface of the sample prepared in Example 4. This suggests that Compound 1-1 has bonded to the surface of the ITO film in Example 4.

TABLE 2

| Sample | Indium | Oxygen | Tin | Nitrogen | Carbon | Silicon | Total |
|---|---|---|---|---|---|---|---|
| Example 4 | 47.2 | 37.2 | 5.9 | 0.8 | 8.4 | 0.5 | 100.0 |
| Untreated ITO glass | 50.6 | 39.7 | 6.2 | 0.3 | 3.1 | 0.1 | 100.0 |

(unit: atomic %)

Example 5

Preparation of an ITO glass having N,N'-bis(m-diisopropylhydroxysilylphenyl)-N,N'-diphenylbenzidine [Compound (1-10)] bonded to the surface thereof The N,N'-bis(m-diisopropylhydroxysilylphenyl)-N,N'-diphenylbenzidine synthesized in Example 2 was mixed with acetonitrile to prepare a colorless and transparent 0.5 mM acetonitrile solution. An ITO (indium tin oxide) film-coated glass having an ITO film surface subjected to an UV ozone treatment for 10 minutes was dipped in the resulting acetonitrile solution for 5 minutes and then withdrawn. The solvent was thereafter evaporated. Next, after the resulting ITO film-coated glass was heated for 30 minutes on a hot plate of 180° C., it was cooled to room temperature. Ultrasonic cleaning was carried out in 0.25 mmol/L sulfuric acid/ethanol for 15 minutes to remove the compound which had not bonded to the substrate. Ultrasonic cleaning was performed for further 5 minutes in ethanol and nitrogen was sprayed to it at room temperature to dry it.

The results of XPS measurement on the surface of the resulting ITO film-coated glass are shown in Table 3. In Table 3, the term "untreated ITO glass" means an ITO film-coated glass having an ITO film surface subjected to an UV ozone treatment and not subjected to a treatment of bonding Compound 1-10 to the surface. Compared with the untreated ITO glass, ratios of nitrogen, carbon, and silicon derived from Compound 1-10 increase and a ratio of indium derived from ITO decreases on the surface of the ITO film-coated glass prepared in Example 5. This suggests that Compound 1-10 has bonded to the surface of the ITO film in Example 5.

TABLE 3

| Sample | Indium | Oxygen | Tin | Nitrogen | Carbon | Silicon | Total |
|---|---|---|---|---|---|---|---|
| Example 5 | 34.6 | 44.1 | 5.4 | 1.2 | 13.7 | 1.0 | 100.0 |
| Untreated ITO glass | 50.6 | 39.7 | 6.2 | 0.3 | 3.1 | 0.1 | 100.0 |

(unit: atomic %)

The silanol-containing triarylamine derivative according to the present invention is useful as a hole transporting material of electrophotographic photoreceptors or organic electroluminescent elements.

The invention claimed is:

1. A silanol-containing triarylamine derivative represented by formula (1):

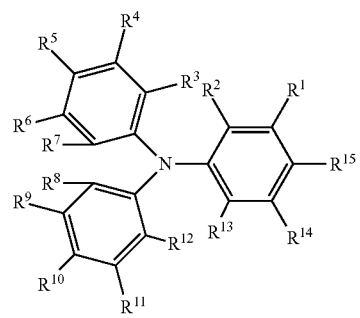

wherein, $R^1$ to $R^{15}$ each independently represents a substituent selected from diarylamino groups represented by formula (2), linear, branched or cyclic monovalent hydrocarbon groups (which may contain the diarylamino group represented by the formula (2) as a substituent) having from 1 to 20 carbon atoms selected from the group consisting of: methyl, ethyl, propyl, isopropyl, butyl, pentyl, hexyl, heptyl, octyl, nonyl, decyl, isobutyl, tert-butyl, cyclopropyl, cyclobutyl, cyclopentyl, cyclohexyl, vinyl, allyl, propenyl, butenyl; phenyl, tolyl; 2-phenylethyl, 3-phenylpropyl, and 4-phenylbutyl, alkoxy groups having from 1 to 20 carbon atoms, aryloxy groups having from 6 to 20 carbon atoms, halogen atoms, a hydrogen atom, and an amino group, with the proviso that at least one of $R^1$, $R^4$, $R^6$, $R^9$, $R^{11}$, and $R^{14}$ is a substituent represented by the following formula: $SiR^{16}R^{17}OH$ wherein, $R^{16}$ and $R^{17}$ each independently represents a linear, branched, or cyclic monovalent hydrocarbon group having from 1 to 20 carbon atoms selected from the group consisting of methyl, ethyl, propyl, isopropyl, butyl, pentyl, hexyl, heptyl, octyl, nonyl, decyl, isobutyl, tert-butyl, cyclopropyl, cyclobutyl, cyclopentyl, cyclohexyl, vinyl, allyl, propenyl, butenyl; phenyl, tolyl; 2-phenylethyl, 3-phenylpropyl, and 4-phenylbutyl,

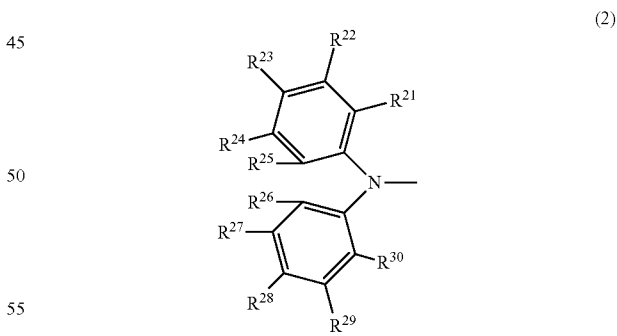

wherein, $R^{21}$, $R^{23}$, $R^{25}$, $R^{26}$, $R^{28}$, and $R^{30}$ each independently represents a substituent selected from linear, branched, or cyclic monovalent hydrocarbon groups having from 1 to 20 carbon atoms selected from the group consisting of: methyl, ethyl, propyl, isopropyl, butyl, pentyl, hexyl, heptyl, octyl, nonyl, decyl, isobutyl, tert-butyl, cyclopropyl, cyclobutyl, cyclopentyl, cyclohexyl, vinyl, allyl, propenyl, butenyl; phenyl, tolyl; 2-phenylethyl, 3-phenylpropyl, and 4-phenylbutyl, alkoxy groups having from 1 to 20 carbon atoms, aryloxy groups having from 6 to 20 carbon atoms, halogen atoms, a hydrogen atom, and an amino group; $R^{22}$, $R^{24}$, $R^{27}$, and $R^{29}$ each independently represents a substituent selected from linear, branched, or cyclic monovalent hydrocarbon groups having from 1 to 20 carbon atoms selected from the group consisting of: methyl, ethyl, propyl, isopropyl, butyl, pentyl, hexyl, heptyl, octyl, nonyl, decyl, isobutyl, tert-butyl, cyclopropyl, cyclobutyl, cyclopentyl, cyclohexyl, vinyl, allyl, propenyl, butenyl; phenyl, tolyl; 2-phenylethyl, 3-phenylpropyl, and 4-phenylbutyl, alkoxy groups having from 1 to 20 carbon atoms, aryloxy groups having from 6 to 20 carbon atoms, halogen atoms, a hydrogen atom, an amino group, and substituents represented by $SiR^{16}R^{17}OH$; with the proviso that without $R^{25}$ and $R^{26}$, carbon atoms at ortho positions with respect to the nitrogen atom may be coupled to form a carbazole ring structure.

2. A process for preparing the silanol-containing triarylamine derivative as claimed in claim 1, comprising steps of: reacting a compound represented by formula (3):

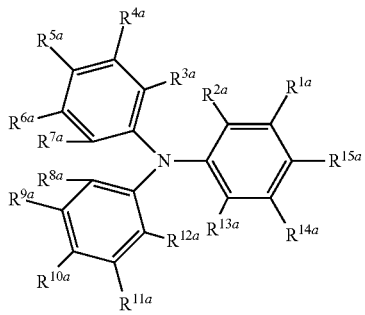

(3)

wherein, $R^{1a}$ to $R^{15a}$ have the same meanings as $R^1$ to $R^{15}$ in the formula (1), respectively, with the proviso that when any of $R^1$ to $R^{15}$ has a substituent represented by $SiR^{16}R^{17}OH$, $R^{1a}$ to $R^{15a}$ corresponding thereto contains a halogen atom instead of $SiR^{16}R^{17}OH$ with a metal or an organic metal; and reacting the reaction product thus obtained with a silicon reagent.

3. An intermediate product of the silanol-containing triarylamine derivative as claimed in claim 1, which is represented by formula (4):

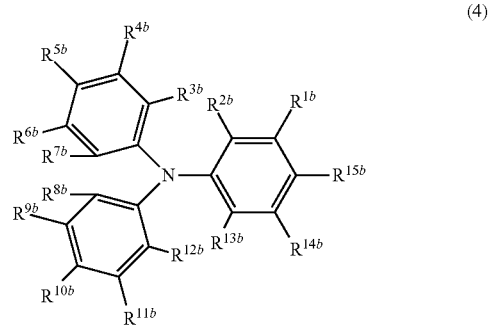

(4)

wherein, $R^{1b}$ to $R^{15b}$ have the same meanings as $R^1$ to $R^{15}$ in the formula (1), respectively, with the proviso that when any of $R^1$ to $R^{15}$ has a substituent represented by $SiR^{16}R^{17}OH$, $R^{1b}$ to $R^{15b}$ corresponding thereto contains $SiR^{16}R^{17}X$ (X=Cl or H) instead of $SiR^{16}R^{17}OH$.

4. An inorganic composite material obtained by bonding the silanol-containing triarylamine derivative as claimed in claim 1 to the surface of an inorganic material.

5. The inorganic material according to claim 4, wherein the inorganic material is a transparent conductive oxide.

6. A preparation process for an inorganic composite material, comprising a step of contacting the silanol-containing triarylamine derivative as claimed in claim 1 with the inorganic material.

7. An inorganic composite material obtained by bonding the silanol-containing triarylamine derivative as claimed in claim 1 to the surface of an inorganic material.

8. The inorganic material according to claim 7, wherein the inorganic material is a transparent conductive oxide.

* * * * *